(12) United States Patent
Shimizu et al.

(10) Patent No.: US 8,668,995 B2
(45) Date of Patent: Mar. 11, 2014

(54) FLUOROPOLYETHER COMPOUND, LUBRICANT AND MAGNETIC DISK EACH CONTAINING THE SAME

(75) Inventors: Tsuyoshi Shimizu, Kobe (JP); Nagayoshi Kobayashi, Kobe (JP)

(73) Assignee: Moresco Corporation, Kobe (JP)

( * ) Notice: Subject to any disclaimer, the term of this patent is extended or adjusted under 35 U.S.C. 154(b) by 0 days.

(21) Appl. No.: 13/487,443

(22) Filed: Jun. 4, 2012

(65) Prior Publication Data

US 2012/0315504 A1    Dec. 13, 2012

Related U.S. Application Data

(60) Provisional application No. 61/497,304, filed on Jun. 15, 2011.

(30) Foreign Application Priority Data

Jun. 13, 2011  (JP) ................................. 2011-131519
Apr. 27, 2012  (JP) ................................. 2012-102551

(51) Int. Cl.
*G11B 5/66*    (2006.01)

(52) U.S. Cl.
USPC ......... 428/835.8; 570/127; 508/580; 508/582

(58) Field of Classification Search
None
See application file for complete search history.

(56) References Cited

U.S. PATENT DOCUMENTS

2012/0251843 A1*   10/2012   Yan et al. ................ 428/800
2013/0209837 A1*   8/2013    Sagata et al. ............ 428/833

FOREIGN PATENT DOCUMENTS

JP    2006-070173 A    3/2006
JP    2010-086598 A    4/2010

OTHER PUBLICATIONS

English Machine translation of JP 2009-270093, Japan, Nov. 2009.*
English Machine translation of JP 2010-086598, Japan, Sep. 2008.*
Kasai, Paul, "Perfluoropolyethers: Intramolecular Disproportionation", Macromolecules, 1992, pp. 6791-6799, vol. 25.
Tagawa, Norio et al., "Spreading of Novel Cyclotriphosphazine-Terminated PFPE Films on Carbon Surfaces", Journal of Tribology, Oct. 2004, pp. 751-754, vol. 126.

* cited by examiner

*Primary Examiner* — Holly Rickman
(74) *Attorney, Agent, or Firm* — Westerman, Hattori, Daniels & Adrian, LLP

(57) ABSTRACT

A compound of the formula (1), lubricant containing the compound and magnetic disk $$C_6H_4-(O-Z-R-X)_2 \quad (1)$$

wherein Z is $-CH_2CH_2O-$ or $-CH_2CH(OH)CH_2O-$, R is $-CH_2CF_2CF_2CF_2O(CF_2CF_2CF_2CF_2O)_nCF_2CF_2CF_2CH_2-$, n is a real number of 0 to 20, X is $-OH$, $-O(CH_2)_mOH$, $-OCH_2CH(OH)CH_2OH$, $-OCH_2CH(OH)CH_2O-C_6H_5$ or $-OCH_2CH(OH)CH_2O-C_6H_4-OCH_3$, m is an integer of 1 to 6.

6 Claims, 1 Drawing Sheet

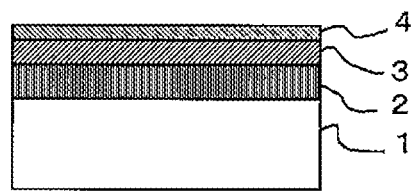

FLUOROPOLYETHER COMPOUND, LUBRICANT AND MAGNETIC DISK EACH CONTAINING THE SAME

CROSS-REFERENCE TO RELATED APPLICATIONS

The present application is based on and claims priority of Japanese patent application Nos. 2011-131519 and 2012-102551 filed on Jun. 13, 2011 and Apr. 27, 2012, respectively. The application also claims priority under 35 U.S.C. §119(e) of Provisional Application No. 61/497,304, filed Jun. 15, 2011. The entire contents of all are hereby incorporated by reference.

TECHNICAL FIELD

The present invention relates to fluoropolyether compounds having an aromatic group and hydroxyl, lubricants containing the compound and magnetic disks having the lubricant applied thereto.

BACKGROUND ART

With an increase in the recording density of magnetic disks, the distance between the magnetic disk serving as a recording medium and the head for use in recording of information or playback has become almost nil close to contact therebetween. The magnetic disk is provided over the surface thereof with a carbon protective film or lubricant film for the purpose of diminishing abrasion due to the contact or sliding of the head thereon or preventing contamination of the disk surface.

The carbon protective film is produced generally by the sputtering process or CVD process. The disk surface is protected with the two films, i.e., the carbon protective film and the lubricant film thereover.

The lubricants generally in use are fluoropolyethers having functional groups. Examples of functional groups are hydroxyl, amino and cyclophosphazene groups. Examples of these lubricants include Fomblin ZTETRAOL manufactured by Solvay Solexis Inc. and having hydroxyl at the terminals of the molecule and PHOSFAROL A20H manufactured by MORESCO Corporation, and having hydroxyl at one terminal of the molecule and a cyclophosphazene group at the other terminal thereof. Further proposed are lubricants having hydroxyl at a molecular terminal and also in the molecular chain (Patent Literature 1).

Fomblin ZTETRAOL exhibits good adsorption to the disk due to the presence of hydroxyl positioned at the opposite terminals of the molecule and is capable of retaining the film of lubricant without permitting spattering even if the disk is rotated at a high speed. Described in Patent Literature 1 is the influence of the film thickness of the lubricant on the spacing between the head and the disk. The spacing can be effectively diminished by reducing the mono-layer thickness of the lubricant. This leads to the proposal that lubricants can be reduced in mono-layer thickness when having hydroxyl at a molecular terminal and also in the molecular chain. This technique makes it possible to diminish the lubricant in the mono-layer thickness.

However, such fluoropolyether compounds are low in durability against Lewis acids and react with $Al_2O_3$ in component members of the head to cut the main chain (see, for example, Nonpatent Literature 1). If this cutting proceeds, the compound becomes lower in molecular weight and eventually evaporates off and disappears from the disk surface, failing to maintain the lubricant film in the case of systems wherein the head moves in contact with or slides on the disk.

Lubricants have been proposed which exhibit improved characteristics to adsorb to the protective layer over the lubricant and have high durability against the environment wherein the magnetic head is levitated at a low level for a rapidly increasing ever-higher recording density. Heretofore proposed as such lubricants are those containing a compound wherein perfluoropolyether groups having a perfluoropolyether main chain and hydroxyl at a terminal are connected to each other by a connecting group having hydroxyl in the structure (Patent Literature 2). Nevertheless, Patent Literature 2 discloses no substantial examples but merely states that the exemplified compound is reacted under a base condition to thereby merely produce the exemplified lubricant compound, is mute about the particular diepoxy compound used and no where is there disclosed any data, such as NMR, for specifying the product.

Patent Literature 1: JP2006-70173A
Patent Literature 2: JP2010-86598A
Nonpatent Literature 1: Macromolecules, 1992, vol. 25, p6791-6799
Nonpatent Literature 2: Journal of Tribology, October 2004, vol. 126, p751

An object of the present invention is to provide a stabilized compound which remains free of decomposition even if brought into contact with the head and is capable of diminishing the spacing between the head and the disk, lubricants comprising the compound, and magnetic disks.

SUMMARY OF THE INVENTION

The present invention provides the following.

1. A compound of the formula (1)

$$C_6H_4-(O-Z-R-X)_2 \qquad (1)$$

wherein Z is $-CH_2CH_2O-$ or $-CH_2CH(OH)CH_2O-$, R is $-CH_2CF_2CF_2CF_2O(CF_2CF_2CF_2CF_2O)_nCF_2CF_2CF_2CH_2-$, n is a real number of 0 to 20, X is $-OH$, $-O(CH_2)_mOH$, $-OCH_2CH(OH)CH_2OH$, $-OCH_2CH(OH)CH_2O-C_6H_5$ or $-OCH_2CH(OH)CH_2O-C_6H_4-OCH_3$, m is an integer of 1 to 6.

2. A lubricant containing a compound of the formula (1).

3. A magnetic disk comprising at least a recording layer and a protective layer formed over a substrate, and a lubricating layer formed over the resulting surface, the lubricating layer containing a compound of the formula (1).

EFFECT OF THE INVENTION

The fluoropolyether compounds of the invention having an aromatic group and hydroxyl are lubricants which solve the two problems of a reduction in mono-layer thickness and resistance to decomposition at the same time. The magnetic disk having the compound of the invention applied thereto enables a reduction in the spacing between the head and the disk, further exhibiting high durability when the head is brought into contact with or slidingly moved on the disk.

EMBODIMENT OF PRACTICING THE INVENTION

Process for Preparing the Lubricant

The lubricant of the formula (I) according to the invention is obtained by reacting, for example, a straight-chain fluoropolyether (a) having hydroxyl at one terminal and an ester group or silyl or alkoxyl at the other terminal with a phenoxy compound having at least two epoxy groups such as Compound (b1), Compound (c1) or Compound (d1), or a phenoxy compound having at least two haloethyl groups such as Compound (b2), Compound (c2) or Compound (d2). [These phenoxy compounds will sometimes be referred to as "compound (B)."] Stated more specifically, the compound is prepared by the following process.

(1) Preparation of Straight-Chain Fluoropolyether (a) Having Hydroxyl at One Terminal and an Ester Group, Silyl Group or Alkoxyl Group at the Other Terminal A straight-chain fluoropolyether (e) having hydroxyl at opposite terminals is reacted with a compound (f) reactive with hydroxyl to produce an ester group or silyl group or alkoxyl group. The reaction temperature is 10 to 60° C., preferably 20 to 40° C. The reaction time is 2 to 20 hours, preferably 10 to 15 hours. The compound (f) is used preferably in an amount of 0.5 to 1.5 equivalents relative to the fluoropolyether (e). A reaction promoting agent may be used. The reaction mixture is thereafter purified, for example, by column chromatography to obtain a straight-chain fluoropolyether (a) having hydroxyl at one terminal and an ester group, silyl group or alkoxyl group at the other terminal. The reaction may be conducted in a solvent. As a solvent are used, for example, dimethyl formamide, 1,4-dioxane, dimethyl sulfoxide and dimethyl acetamide. Examples of the reaction promoting agents are imidazole, pyridine and sodium hydride.

The fluoropolyether (e) having hydroxyl at opposite terminals can be, for example, a compound of the formula

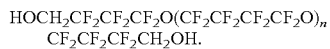
$HOCH_2CF_2CF_2CF_2O(CF_2CF_2CF_2CF_2O)_n$
$CF_2CF_2CF_2CH_2OH.$

The fluoropolyether is 300 to 2000, preferably 400 to 1200, more preferably 500 to 800, in number average molecular weight. The number average molecular weight mentioned is a value measured by $^{19}F$-NMR using JNM-ECX400, product of JEOL Ltd. For NMR measurement, the sample itself was used without dilution with a solvent. As a reference for chemical shift, a known peak was used which is a portion of fluoropolyether skeleton structure.

n is a real number of 0 to 20, preferably 0 to 10, more preferably 0 to 4, particularly preferably 1 to 3, most preferably 1 to 2.

The fluoropolyether (e) is a compound having a molecular weight distribution. The molecular weight distribution (PD), which is weight average molecular weight/number average molecular weight, is 1.0 to 1.5, preferably 1.0 to 1.3, and more preferably 1.0 to 1.1. The molecular weight distribution is a characteristic value obtained by using HPLC-8220GPC, product of Tosoh Co., Ltd., column (PLgel Mixed E), product of Polymer Laboratories, eluent which is HCFC-type alternative CFC and a non-functional perfluoropolyether serving as a reference material.

Examples of compounds (f) reactive with hydroxyl for forming an ester group or silyl group or alkoxyl group are acid anhydrides, silyl halides, alkyl halides, etc.

Examples of acid anhydrides are maleic anhydride, succinic anhydride and phthalic anhydride, and a compound represented by $R^aOR^b$ ($R^a$ and $R^b$ are the same or different and are $CH_3CO$, $PhCO$, $CH_3SO_2$, $PhSO_2$, $CF_3CH_2CO$ or $CH_2C_6H_4SO_2$, Ph is phenyl). Concrete examples of compounds represented by $R^aOR^b$ are trifluoromethylacetic anhydride, benzoic anhydride, p-toluenesulfonic anhydride, trifluoromethanesulfonic anhydride, acetic anhydride, maleic anhydride, succinic anhydride, phthalic anhydride, acetic benzoic anhydride, methanesulfonic anhydride and benzenesulfonic anhydride.

Examples of silyl halides are compounds represented by $(R^c)_3SiY$, $R^d(R^e)_2SiY$ and $R^dR^eR^gSiY$ ($R^c$ is alkyl having 1 to 4 carbon atoms or phenyl, $R^d$ is alkyl having 1 to 18 carbon atoms, alkoxy having 1 to 4 carbon atoms, phenyl, benzyl, pentafluorophenyl, cyanopropyl or vinyl, $R^e$ is alkyl having 1 to 2 carbon atoms or phenyl, $R^g$ is alkyl having 1 to 4 carbon atoms substituted by phenyl). Concrete examples are trimethylsilyl chloride, triethylsilyl chloride, triisopropylsilyl chloride, t-butyl-dimethylsilyl chloride, t-butyldiphenylsilyl chloride, (3-cyanopropyl)dimethylchlorosilane, benzylchlorodimethylsilane, butyldimethylchlorosilane, chloro(decyl) dimethylsilane, chloro(dodecyl)dimethylsilane, chlorodimethyl(3-phenylpropyl)silane, chlorodimethylphenylsilane, chlorodimethylpropylsilane, chlorodimethylvinylsilane, diethylisopropylsilyl chloride, dimethyl-n-octylchlorosilane, dimethylethylsilyl chloride, dimethylisopropylchlorosilane, dimethyloctadecylchlorosilane, diphenylmethylchlorosilane, methyloctadecyl(3-phenylpropyl)-chlorosilane, pentafluorophenyldimethylchlorosilane, t-butoxy-diphenylchlorosilane, t-butyldiphenylchlorosilane and triphenylchlorosilane.

Examples of alkyl halides are a compound represented by AY (A is alkyl having 1 to 5 carbon atoms, Y is a halogen such as chlorine, bromine and iodine). Concrete examples are chloromethane, bromomethane, iodomethane, chloroethane, bromoethane, iodoethane, 1-bromopropane, 2-bromopropane, 1-iodopropane, 2-iodopropane, 1-bromo-2-methylpropane, 1-bromobutane, 2-bromo-2-methylpropane, 2-bromobutane, 1-iodo-2-methylpropane, 1-iodobutane, 2-iodo-2-methylpropane, 2-iodobutane, 1-iodo-2-methylbutane, 1-iodo-3-methylbutane, 1-bromo-3-methylbutane, 1-bromopentane, 2-bromo-2-methylbutane and 3-bromopentane.

For example, $HOCH_2CF_2CF_2CF_2O(CF_2CF_2CF_2CF_2O)_n$ $CF_2CF_2CF_2CH_2OH$ is used as compound (e), and acetic anhydride is used as compound (f). The reaction between these two compounds produces $CH_3COOCH_2CF_2CF_2CF_2O$ $(CF_2CF_2CF_2CF_2O)_nCF_2CF_2CF_2CH_2OH$ and $CH_3COOH$, and the former compound is compound (a).

Further in the case where trimethylsilyl chloride is used as compound (f), the compound (a) produced is $(CH_3)_3$ $SiOCH_2CF_2CF_2CF_2O(CF_2CF_2CF_2CF_2O)_nCF_2CF_2CF_2CH_2$ OH.

(2) Preparation of Lubricant of the Invention

The fluoropolyether (a) obtained above is reacted with a phenoxy compound (B) having at least two epoxy groups or at least two haloethyl groups in the presence of a catalyst or alkali metal. Examples of haloethyl groups are chloroethyl, bromoethyl or idoethyl. The reaction temperature is 50 to 100° C., preferably 70 to 90° C. The reaction time is 20 to 100 hours, preferably 50 to 80 hours. It is desirable to use the compound (B) in an amount of 0.2 to 1.0 equivalent and the catalyst in an amount of 0.05 to 0.1 equivalent, relative to the compound (a). The catalysts to be used are alkali compounds such as sodium tert-butoxide, potassium tert-butoxide and sodium hydride. The alkali metals to be used are, for example, sodium and potassium. The reaction may be conducted in a solvent. Examples of solvents to be used are tert-butanol, toluene, xylene and the like. The reaction mixture is thereafter washed, for example, with water and dewatered. The protective group, such as ester group or silyl or alkoxyl remaining at one terminal of the perfluoropolyether is thereafter removed as by hydrolysis for deprotection, whereby a compound (I) of the invention wherein X is —OH is obtained. Deprotection promoting agents can be used which include tetrabutylammonium fluoride, potassium fluoride and sodium fluoride.

Examples of compound (B) are shown below. Compound (b1) is 1,3-bis(glycidyloxy)benzene. 1,2-Bis(glycidyloxy)

benzene and 1,4-bis(glycidyloxy)benzene are also usable. Compound (b2) is 1,4-bis(2-bromoethoxy)benzene. 1,2- and 1,3-isomers are also usable.

Compound (c1) is bis(4-glycidyloxyphenyl)methane. Compound (c2) is bis(4-bromoethoxyphenyl)methane.

Compound (d1) is tris(4-glycidyloxyphenyl)methane. Compound (d2) is tris(4-bromoethoxyphenyl)methane.

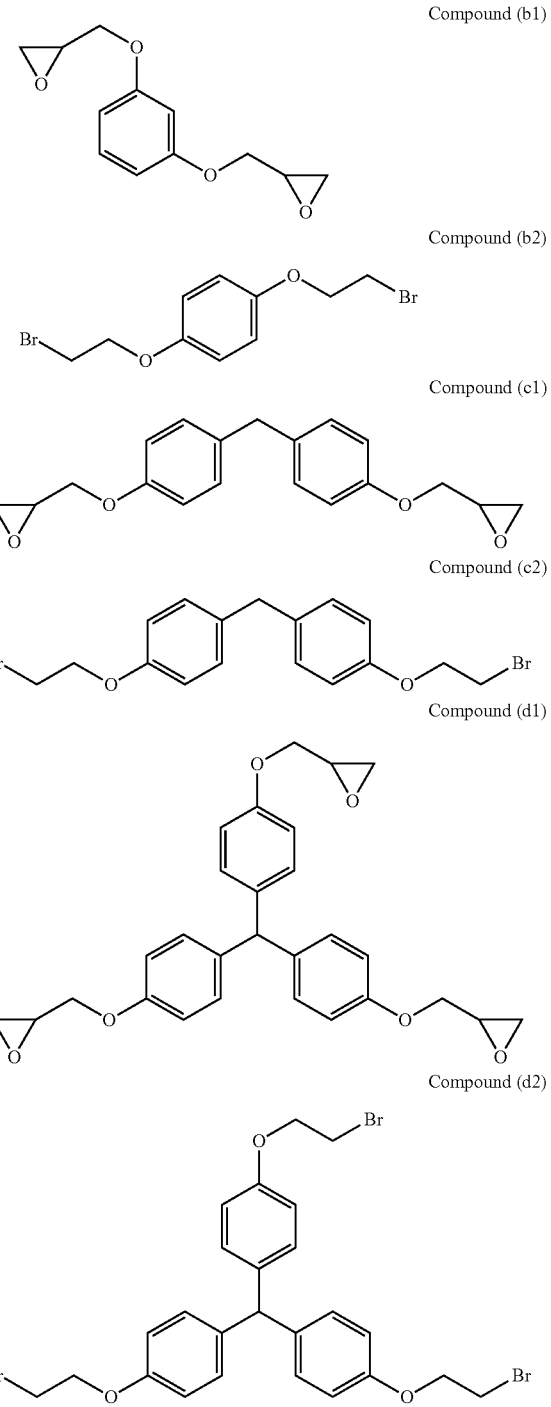

This compound wherein X is —OH is reacted with an alkali metal and a haloalcohol of the formula Y(CH$_2$)mOH [wherein Y is chlorine, bromine, iodine or like halogen, and m is an integer of 1 to 6], whereby a compound (1) of the invention in which X is —O(CH$_2$)mOH is obtained. m is preferably 1 to 4, more preferably 2 to 4. Sodium, potassium or the like can be used as the alkali metal.

A compound (1) of the invention wherein X is —OCH$_2$CH(OH)CH$_2$OH is obtained by reacting glycidol with the compound wherein X is —OH in the presence of a catalyst.

A compound (1) of the invention wherein X is —OCH$_2$CH(OH)CH$_2$O—C$_6$H$_5$ is obtained by reacting glycidyl phenyl ether with the compound wherein X is —OH in the presence of a catalyst.

A compound (1) of the invention wherein X is —OCH$_2$CH(OH)CH$_2$O—C$_6$H$_4$—OCH$_3$ is obtained by reacting glycidyl 4-methoxy phenyl ether with the compound wherein X is —OH in the presence of a catalyst.

These reactions may be conducted at a temperature of 50 to 100° C., preferably 70 to 90° C. The reaction time is 20 to 100 hours, preferably 50 to 80 hours. These reactions may be conducted in a solvent. Based on the hydroxyl of the compound (1) of the invention wherein X is —OH, it is desirable to use 1.0 to 2.0 equivalents of the alkali metal, 0.05 to 0.1 equivalent of the catalyst, or 1.0 to 2.0 equivalents of Y(CH$_2$)mOH, glycidol, glycidyl phenyl ether or glycidyl 4-methoxy phenyl ether. The reaction mixture is thereafter washed with water, dewatered and purified by silica gel chromatography, whereby the desired compound is obtained as a fraction.

The compound of the present invention is applied to the magnetic disk surface preferably by diluting the compound with a solvent and coating the disk surface with the diluted compound. Examples of useful solvents are PF-5060, PF-5080, HFE-7100 and HFE-7200 manufactured by 3M, Vertrel-XF, product of DuPont, etc. The concentration of the compound as diluted is up to 1 wt. %, preferably 0.001 to 0.1 wt. %.

While the compound of the invention is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd., Krytox manufactured by DuPont, or the like.

The compound of the present invention enables the head to be spaced by a small distance from the magnetic disk inside magnetic disk devices and is useful as a lubricant for giving improved durability under a sliding condition. The compound of the invention is characterized by the interaction of the hydroxyl at the terminal of the molecule with the polar site present in the carbon protective film and by the interaction of the aromatic group in the molecular chain with carbon unsaturated bonds present in the carbon protective film. Accordingly, the compound is usable as a surface protective film for magnetic heads, photomagnetic recording devices, magnetic tapes, plastics and like organic materials having a carbon protective film, and also as a surface protective film for inorganic materials such as glass and metal.

FIG. 1 shows a sectional view schematically showing the magnetic disk of the invention. The magnetic disk of the invention comprises a substrate 1, at least one recording layer 2 formed on the substrate 1, a protective layer 3 on the recording layer 2 and a lubricant layer 4 formed thereon, as an outermost layer, which contains the compound of the invention. The substrate is composed of aluminum alloy, glass and like ceramics, polycarbonate or the like.

The recording layer of the magnetic disk, i.e., the magnetic layer is composed of mainly elements capable of forming ferromagnetic bodies, such as iron, cobalt or nickel, alloy or oxide containing chromium, platinum or tantalum in addition to such elements. These materials are applied by, e.g., a plating method or a sputtering method. The protective layer is formed of carbon, SiC, SiO$_2$ or the like. The layer is formed by a sputtering method or CVD method.

Lubricant layers presently available are up to 30 Å in thickness, so that when a lubricant having a viscosity of higher than about 100 mPa·s at 20° C. is applied as it is, the resulting film is likely to have an excessively large thickness. Accordingly the lubricant for use in coating is used as dissolved in a solvent. When the compound of the present invention is applied as dissolved in a solvent, the film thickness to be obtained is easy to control in the case where the present compound serves singly as a lubricant and also in the case where the compound is used as mixed with other lubricant. The concentration varies with the method and conditions of application, mixing ratio, etc. The lubricant film of the present invention is preferably 5 to 15 Å in thickness.

In order to assure the lubricant of improved adhesion to the ground layer, the lubricant applied can be subjected to heat treatment or ultraviolet treatment. The heat treatment is conducted at 60 to 150° C., preferably at 80 to 150° C. The ultraviolet treatment is conducted using ultraviolet rays of 185 nm and 254 nm in main wavelength.

The magnetic disk of the invention can be applied to a magnetic disk apparatus which can accommodate the disk and which is provided with a magnetic disk drive including a head for recording, reproducing and erasing information and a motor for rotating the disk; and with a control system for controlling the drive.

The magnetic disk of the invention and the magnetic disk apparatus produced using the magnetic disk thereof can be applied for the following: electronic computers, and outer memories for word processors; and can be also applied in navigation systems, games, cellular phone, PHS (personal handyphone system) and like instruments and machines and inner and outer memories for prevention of crimes in buildings, and for management/control systems of power plants.

BRIEF DESCRIPTION OF THE DRAWING

FIG. 1 is a section view showing the structure of the magnetic disk of the invention.

EXAMPLES

The invention will be described in more detail with reference to the following examples to which, however, the invention is not limited. $^{19}$F-NMR (solvent: none, reference material: $OCF_2CF_2CF_2CF_2O$ in the obtained product being taken as −125.8 ppm): $^1$H-NMR (solvent: none, reference material: $D_2O$).

Example 1

Preparation of HO—R—$OCH_2CH(OH)CH_2O$—$C_6H_4$—O—$CH_2CH(OH)CH_2$—O—R—OH (Compound 1)

R is —$CH_2CF_2CF_2CF_2O(CF_2CF_2CF_2CF_2O)_nCF_2CF_2CF_2CH_2$—

Dimethylformaldehyde (50 g), 100 g of a fluoropolyether of the formula $HOCH_2CF_2CF_2CF_2O(CF_2CF_2CF_2CF_2O)_nCF_2CF_2CF_2CH_2OH$ wherein n is 1.5 and which is 700 in number average molecular weight and 1.15 in molecular weight distribution, triisopropylsilyl chloride (25 g) and imidazole (11 g) were stirred at 30° C. in an argon atmosphere for 12 hours. The mixture was thereafter washed with water, dewatered and purified by silica gel chromatography, affording 56 g of compound (a1) having one hydroxyl group at one terminal and a triisoprolylsilyl group at the other terminal. This compound (a1, 56 g) was dissolved in a tert-butanol (28 g), a compound (7 g) of the formula (b1) and potassium tert-butoxide (0.4 g) were added to the solution, and the mixture was stirred at 70° C. for 80 hours. The mixture was thereafter washed with water, 1 M tetrahydrofuran solution (52 ml) of tetrahydrobutylammonium fluoride was admixed with the mixture, followed by purification by column chromatography, giving 41 g of compound 1.

Compound 1 was a colorless transparent liquid and 1.75 g/cm$^3$ in density at 20° C. Compound 1 was identified by NMR with the result shown.

$^{19}$F-NMR (solvent: none, reference material: $OCF_2CF_2CF_2CF_2O$ in the obtained product being taken as −125.8 ppm):
δ=−83.5 ppm
[18F, —$OCF_2CF_2CF_2CF_2O$—],
δ=−123.3 ppm
[4F, —$OCF_2CF_2CF_2CH_2OCH_2CH(OH)CH_2$—O—$C_6H_4$—],
δ=−120.3 ppm
[4F, —$OCF_2CF_2CF_2CH_2OH$],
δ=−125.8 ppm
[10F, —$OCF_2CF_2CF_2CF_2O$—],
δ=−127.1 ppm
[4F, —$OCF_2CF_2CF_2CH_2OH$],
δ=−127.6 ppm
[4F, —$OCF_2CF_2CF_2CH_2OCH_2CH(OH)CH_2$—$C_6H_4$—],
n=1.3
$^1$H-NMR (solvent: none, reference material: $D_2O$)
δ=3.2~3.8 ppm
[22H, $HOCH_2CF_2CF_2CF_2O$—, —$OCF_2CF_2CF_2CH_2OCH_2CH(OH)CH_2$—O—$C_6H_4$—],
δ=6.1 ppm, 6.7 ppm
[4H, —$OCF_2CF_2CF_2CH_2OCH_2CH(OH)CH_2$—$C_6H_4$—].

Example 2

Preparation of $HOCH_2CH(OH)CH_2O$—R—$OCH_2CH(OH)CH_2$—O—$C_6H_4$—O—$CH_2CH(OH)CH_2O$—R—$OCH_2CH(OH)CH_2OH$ (Compound 2)

R is —$CH_2CF_2CF_2CF_2O(CF_2CF_2CF_2CF_2O)_nCF_2CF_2CF_2CH_2$—

The compound 1 (10 g) obtained in Example 1 was dissolved in tert-butanol (5 g), glycidol (1.2 g) and potassium tert-butoxide (0.1 g) were added to the solution, and the mixture was stirred at 70° C. for 80 hours. The resulting mixture was washed with water and purified by column chromatography, whereby 6 g of compound 2 was obtained.

Compound 2 was a colorless transparent liquid and 1.69 g/cm$^3$ in density at 20° C. Compound 2 was identified by NMR with the result shown.

$^{19}$F-NMR
δ=−83.5 ppm
[19F, —$OCF_2CF_2CF_2CF_2O$—],
δ=−120.3 ppm
[8F, $HOCH_2CH(OH)CH_2OCH_2CF_2CF_2CF_2O$—, —$OCF_2CF_2CF_2CH_2OCH_2CH(OH)CH_2$—O—$C_6H_4$—],
δ=−125.8 ppm
[11F, —$OCF_2CF_2CF_2CF_2O$—],
δ=−127.6 ppm
[8F, $HOCH_2CH(OH)CH_2OCH_2CF_2CF_2CF_2O$—, —$OCF_2CF_2CF_2CH_2OCH_2CH(OH)CH_2$—O—$C_6H_4$—],
n=1.4
$^1$H-NMR (solvent: none, reference material: $D_2O$)
δ=3.2~3.8 ppm
[34H, $HOCH_2CH(OH)CH_2OCH_2CF_2CF_2CF_2O$—, —$OCF_2CF_2CF_2CH_2OCH_2CH(OH)CH_2$—$C_6H_4$—],
δ=6.1 ppm, 6.7 ppm
[4H, —$OCF_2CF_2CF_2CH_2OCH_2CH(OH)CH_2$—O—$C_6H_4$—],

Example 3

Preparation of $HOCH_2CH_2O—R—OCH_2CH(OH)$ $CH_2—O—C_6H_4—O—CH_2CH(OH)CH_2O—R—$ $OCH_2CH_2OH$ (Compound 3)

R is $—CH_2CF_2CF_2CF_2O(CF_2CF_2CF_2CF_2O)_nCF_2CF_2CF_2CH_2—$

The compound 1 (10 g) obtained in Example 1 was dissolved in Vertrel-XF (40 g) manufactured by DuPont, metallic sodium (0.3 g) was added to the solution, followed by stirring with heating at 70° C. for 20 hours. Then, 2-bromoethanol (1.9 g) was added and the mixture was stirred at 70° C. for 60 hours. The resulting mixture was washed with water and purified by column chromatography to give 5 g of compound 3.

Compound 3 was a colorless transparent liquid and 1.72 g/cm³ in density at 20° C. Compound 3 was identified by NMR with the result shown.

$^{19}F$-NMR
$\delta$=−83.5 ppm
[19F, —OC$\underline{F_2}$CF$_2$CF$_2$CF$_2$O—],
$\delta$=−120.3 ppm
[8F, HOCH$_2$CH$_2$OCH$_2$C$\underline{F_2}$CF$_2$CF$_2$O—, —OCF$_2$C$\underline{F_2}$OCH$_2$CH(OH)CH$_2$—O—C$_6$H$_4$—],
$\delta$=−125.8 ppm
[11F, —OCF$_2$C$\underline{F_2}$CF$_2$CF$_2$O—],
$\delta$=−127.6 ppm
[8F, HOCH$_2$CH$_2$OCH$_2$CF$_2$C$\underline{F_2}$CF$_2$O—, —OCF$_2$C$\underline{F_2}$CF$_2$CH$_2$OCH$_2$CH(OH)CH$_2$—O—C$_6$H$_4$—],
n=1.4

$^1H$-NMR (solvent: none, reference material: D$_2$O)
$\delta$=3.2~3.8 ppm
[30H, HOC$\underline{H_2}$C$\underline{H_2}$OC$\underline{H_2}$CF$_2$CF$_2$CF$_2$O—, —OCF$_2$CF$_2$CF$_2$C$\underline{H_2}$OC$\underline{H_2}$C$\underline{H(OH)}$C$\underline{H_2}$—O—C$_6$H$_4$—],
$\delta$=6.1 ppm, 6.7 ppm
[4H, —OCF$_2$CF$_2$CF$_2$CH$_2$OCH$_2$CH(OH)CH$_2$—O—C$_6$$\underline{H_4}$—],

Example 4

Preparation of $H_3CO—C_6H_4—OCH_2CH(OH)$ $CH_2O—R—OCH_2CH(OH)CH_2—O—C_6H_4—O—$ $CH_2CH(OH)CH_2O—R—OCH_2CH(OH)CH_2O—$ $C_6H_4—OCH_3$ (Compound 4)

R is $—CH_2CF_2CF_2CF_2O(CF_2CF_2CF_2CF_2O)_nCF_2CF_2CF_2CH_2—$

The compound 1 (10 g) obtained in Example 1 was dissolved in tert-butanol (5 g), glycidyl 4-methoxy phenyl ether (2.7 g) and potassium tert-butoxide (0.1 g) were added to the solution, and the mixture was stirred at 70° C. for 80 hours. The resulting mixture was washed with water and purified by column chromatography, affording 8 g of compound 4.

Compound 4 was a colorless transparent liquid and 1.67 g/cm³ in density at 20° C. Compound 4 was identified by NMR with the result shown.

$^{19}F$-NMR
$\delta$=−83.5 ppm
[18F, —OC$\underline{F_2}$CF$_2$CF$_2$CF$_2$O—],
$\delta$=−120.3 ppm
[8F, H$_3$COC$_6$H$_4$OCH$_2$CH(OH)CH$_2$OCH$_2$C$\underline{F_2}$CF$_2$CF$_2$O—, —OCF$_2$C$\underline{F_2}$CF$_2$CH$_2$OCH$_2$CH(OH)CH$_2$—O—C$_6$H$_4$—],
$\delta$=−125.8 ppm
[10F, —OCF$_2$C$\underline{F_2}$CF$_2$CF$_2$O—],
$\delta$=−127.6 ppm
[8F, H$_3$COC$_6$H$_4$OCH$_2$CH(OH)CH$_2$OCH$_2$CF$_2$C$\underline{F_2}$CF$_2$O—, —OCF$_2$CF$_2$C$\underline{F_2}$CH$_2$OCH$_2$CH(OH)CH$_2$—O—C$_6$H$_4$—],
n=1.3

$^1H$-NMR (solvent: none, reference material: D$_2$O)
$\delta$=3.1~3.8 ppm
[38H, H$_3$COC$_6$H$_4$OC$\underline{H_2}$CH(OH)C$\underline{H_2}$OC$\underline{H_2}$CF$_2$CF$_2$CF$_2$O—, —OCF$_2$CF$_2$CF$_2$C$\underline{H_2}$OC$\underline{H_2}$C$\underline{H(OH)}$C$\underline{H_2}$—O—C$_6$H$_4$—],
$\delta$=6.1~6.7 ppm
[12H, H$_3$COC$_6$$\underline{H_4}$OCH$_2$CH(OH)CH$_2$OCH$_2$CF$_2$CF$_2$CF$_2$O—, —OCF$_2$CF$_2$CF$_2$CH$_2$OCH$_2$CH(OH)CH$_2$—O—C$_6$$\underline{H_4}$—],

Example 5

Preparation of $HO—R—OCH_2CH_2O—C_6H_4—O—$ $CH_2CH_2—O—R—OH$ (Compound 5)

R is $—CH_2CF_2CF_2CF_2O(CF_2CF_2CF_2CF_2O)_nCF_2CF_2CF_2CH_2—$

The reaction was conducted in the same manner as in Example 1 except that Compound (b2) (10 g) was used in place of Compound (b1) (7 g) and sodium hydride (2.4 g) was used in place of potassium butoxide (0.4 g) to obtain 31 g of Compound 5.

Compound 5 was a white solid. Compound 5 was identified by NMR with the result shown.

$^{19}F$-NMR (solvent: none, reference material: OCF$_2$CF$_2$C$\underline{F_2}$CF$_2$O in the obtained product being taken as −125.8 ppm):
$\delta$=−83.5 ppm
[18F, —OC$\underline{F_2}$CF$_2$CF$_2$CF$_2$O—],
$\delta$=−123.3 ppm
[4F, —OCF$_2$CF$_2$C$\underline{F_2}$CH$_2$OCH$_2$CH$_2$—O—C$_6$H$_4$—],
$\delta$=−120.3 ppm
[4F, —OCF$_2$CF$_2$C$\underline{F_2}$CH$_2$OH],
$\delta$=−125.8 ppm
[10F, —OCF$_2$C$\underline{F_2}$CF$_2$CF$_2$O—],
$\delta$=−127.1 ppm
[4F, —OCF$_2$C$\underline{F_2}$CF$_2$CH$_2$OH],
$\delta$=−127.6 ppm
[4F, —OCF$_2$C$\underline{F_2}$CF$_2$CH$_2$OCH$_2$CH$_2$—O—C$_6$H$_4$—],
n=1.3

$^1H$-NMR (solvent: none, reference material: D$_2$O)
$\delta$=3.2~3.8 ppm
[18H, HOC$\underline{H_2}$CF$_2$CF$_2$CF$_2$O—, —OCF$_2$CF$_2$CF$_2$C$\underline{H_2}$OC$\underline{H_2}$C$\underline{H_2}$—O—C$_6$H$_4$—],
$\delta$=6.8 ppm
[4H, —OCF$_2$CF$_2$CF$_2$CH$_2$OCH$_2$CH$_2$—O—C$_6$$\underline{H_4}$—]

Example 6

Preparation of $HOCH_2CH(OH)CH_2O—R—$ $OCH_2CH_2O—C_6H_4—O—CH_2CH_2—O—R—$ $OCH_2CH(OH)CH_2OH$ (Compound 6)

R is $—CH_2CF_2CF_2CF_2O(CF_2CF_2CF_2CF_2O)_nCF_2CF_2CF_2CH_2—$

The compound 5 (10 g) obtained in Example 5 was dissolved in tert-butanol (5 g), glycidol (1.1 g) and potassium tert-butoxide (0.1 g) were added to the solution, and the mixture was stirred at 70° C. for 80 hours. The resulting mixture was washed with water and purified by column chromatography, whereby 6 g of compound 6 was obtained.

Compound 6 was a white solid. Compound 6 was identified by NMR with the result shown.

$^{19}$F-NMR
δ=−83.5 ppm
[18F, —OC$\underline{F}_2$CF$_2$CF$_2$C$\underline{F}_2$O—],
δ=−120.3 ppm
[8F, HOCH$_2$CH(OH)CH$_2$OCH$_2$C$\underline{F}_2$CF$_2$CF$_2$O—, —OCF$_2$C$\underline{F}_2$CF$_2$CH$_2$OCH$_2$CH$_2$—O—C$_6$H$_4$—],
δ=−125.8 ppm
[10F, —OCF$_2$C$\underline{F}_2$C$\underline{F}_2$CF$_2$O—],
δ=−127.6 ppm
[8F, HOCH$_2$CH(OH)CH$_2$OCH$_2$CF$_2$C$\underline{F}_2$CF$_2$O—, —OCF$_2$C$\underline{F}_2$CF$_2$CH$_2$OCH$_2$CH$_2$—O—C$_6$H$_4$—],
n=1.3

$^1$H-NMR (solvent: none, reference material: D$_2$O)
δ=3.2~3.8 ppm
[30H, HOC$\underline{H}_2$C$\underline{H}$(O$\underline{H}$)C$\underline{H}_2$OC$\underline{H}_2$CF$_2$CF$_2$CF$_2$O—, —OCF$_2$CF$_2$CF$_2$C$\underline{H}_2$OC$\underline{H}_2$C$\underline{H}_2$—C$_6$H$_4$—],
δ=6.8 ppm
[4H, —OCF$_2$CF$_2$CF$_2$CH$_2$OCH$_2$CH(OH)CH$_2$—O—C$_6$$\underline{H}_4$—]

Example 7

Preparation of HOCH$_2$CH$_2$O—R—OCH$_2$CH$_2$O—C$_6$H$_4$—O—CH$_2$CH$_2$—O—R—OCH$_2$CH$_2$OH
(Compound 7)

R is —CH$_2$CF$_2$CF$_2$CF$_2$O(CF$_2$CF$_2$CF$_2$CF$_2$O)$_n$CF$_2$CF$_2$CF$_2$CH$_2$—

The compound 5 (10 g) obtained in Example 5 was dissolved in Vertrel-XF (40 g) manufactured by DuPont, metallic sodium (0.3 g) was added to the solution, followed by stirring with heating at 70° C. for 20 hours. Then, 2-bromoethanol (1.8 g) was added and the mixture was stirred at 70° C. for 60 hours. The resulting mixture was washed with water and purified by column chromatography to give 4 g of compound 7.

Compound 7 was a white solid. Compound 7 was identified by NMR with the result shown.

$^{19}$F-NMR
δ=−83.5 ppm
[18F, —OC$\underline{F}_2$CF$_2$CF$_2$C$\underline{F}_2$O—],
δ=−120.3 ppm
[8F, HOCH$_2$CH$_2$OCH$_2$C$\underline{F}_2$CF$_2$CF$_2$O—, —OCF$_2$C$\underline{F}_2$CF$_2$CH$_2$OCH$_2$CH$_2$—O—C$_6$H$_4$—],
δ=−125.8 ppm
[10F, —OCF$_2$C$\underline{F}_2$C$\underline{F}_2$CF$_2$O—],
δ=−127.6 ppm
[8F, HOCH$_2$CH$_2$OCH$_2$CF$_2$C$\underline{F}_2$CF$_2$O—, —OCF$_2$C$\underline{F}_2$CF$_2$CH$_2$OCH$_2$CH$_2$—O—C$_6$H$_4$—],
n=1.3

$^1$H-NMR (solvent: none, reference material: D$_2$O)
δ=3.2~3.7 ppm
[26H, HOC$\underline{H}_2$C$\underline{H}_2$OC$\underline{H}_2$CF$_2$CF$_2$CF$_2$O—, —OCF$_2$CF$_2$CF$_2$C$\underline{H}_2$OC$\underline{H}_2$C$\underline{H}_2$—O—C$_6$H$_4$—],
δ=6.8 ppm
[4H, —OCF$_2$CF$_2$CF$_2$CH$_2$OCH$_2$CH$_2$—O—C$_6$$\underline{H}_4$—]

Example 8

Preparation of HO—R—OCH$_2$CH$_2$O—C$_6$H$_4$—O—CH$_2$CH$_2$—O—R—OH (Compound 8)

R is —CH$_2$CF$_2$CF$_2$CF$_2$O(CF$_2$CF$_2$CF$_2$CF$_2$O)$_n$CF$_2$CF$_2$CF$_2$CH$_2$—

Dimethylformaldehyde (50 g), 100 g of a fluoropolyether of the formula HOCH$_2$CF$_2$CF$_2$CF$_2$O(CF$_2$CF$_2$CF$_2$CF$_2$O)$_n$CF$_2$CF$_2$CF$_2$CH$_2$OH wherein n is 8.5 and which is 2203 in number average molecular weight and 1.30 in molecular weight distribution, triisopropylsilyl chloride (8 g) and imidazole (4 g) were stirred at 30° C. in an argon atmosphere for 12 hours. The mixture was thereafter washed with water, dewatered and purified by silica gel chromatography, affording 51 g of compound (a2) having one hydroxyl group at one terminal and a triisoprolylsilyl group at the other terminal. This compound (a2, 51 g) was dissolved in a tert-butanol (26 g), a compound (3 g) of the formula (b2) and sodium hydride (1 g) were added to the solution, and the mixture was stirred at 70° C. for 80 hours. The mixture was thereafter washed with water, 1 M tetrahydrofuran solution (17 ml) of tetrahydrobutylammonium fluoride was admixed with the mixture, followed by purification by column chromatography, giving 39 g of compound 8.

Compound 8 was a white solid. Compound 8 was identified by NMR with the result shown.

$^{19}$F-NMR (solvent: none, reference material: OCF$_2$CF$_2$CF$_2$CF$_2$O in the obtained product being taken as −125.8 ppm):
δ=−83.5 ppm
[76F, —OC$\underline{F}_2$CF$_2$CF$_2$C$\underline{F}_2$O—],
δ=−123.3 ppm
[4F, —OCF$_2$CF$_2$C$\underline{F}_2$CH$_2$OCH$_2$CH$_2$—O—C$_6$H$_4$—],
δ=−120.3 ppm
[4F, —OC$\underline{F}_2$CF$_2$CF$_2$CH$_2$OH],
δ=−125.8 ppm
[68F, —OCF$_2$C$\underline{F}_2$C$\underline{F}_2$CF$_2$O—],
δ=−127.1 ppm
[4F, —OCF$_2$C$\underline{F}_2$CF$_2$CH$_2$OH],
δ=−127.6 ppm
[4F, —OCF$_2$C$\underline{F}_2$CF$_2$CH$_2$OCH$_2$CH$_2$—O—C$_6$H$_4$—],
n=8.5

$^1$H-NMR (solvent: none, reference material: D$_2$O)
δ=3.2~3.8 ppm
[18H, HOC$\underline{H}_2$CF$_2$CF$_2$CF$_2$O—, —OCF$_2$CF$_2$CF$_2$C$\underline{H}_2$OC$\underline{H}_2$C$\underline{H}_2$—O—C$_6$H$_4$—],
δ=6.8 ppm
[4H, —OCF$_2$CF$_2$CF$_2$CH$_2$OCH$_2$CH$_2$—O—C$_6$$\underline{H}_4$—]

Example 9

Measurement of Decomposition Resistance to Aluminum Oxide

A sample was used for evaluation which was prepared from each of Compounds 1 to 8, by adding 20 wt. % of Al$_2$O$_3$ to the lubricant, intensely shaking the mixture and thereafter thoroughly agitating the mixture with ultrasonic waves. The sample was checked for decomposition resistance using a thermal analyzer (TG/TDA). The sample was heated at 250° C. for 100 minutes, and the weight reduction of the lubricant was measured. The test was conducted with use of 20 mg of the sample under nitrogen atmosphere. For comparison, 20 mg of each of Lubricants 1 to 8 was thermally analyzed in the same manner as above with the exception of adding no Al$_2$O$_3$.

Example 10

Measurement of Mono-Layer Thickness

As disclosed in Nonpatent Literature 2, the lubricant applied to a magnetic disk can be checked for mono-layer thickness (thickness per molecule) when the diffusion behavior of the lubricant on the disk is observed by an ellipsometer. The mono-layer thickness is obtained as the thickness of a terrace portion of the lubricant film.

Stated more specifically, the compounds 1 to 8 prepared in Examples were respectively dissolved in portions of Vertrel-XF manufactured by DuPont. These solutions contain the respective compounds 1 to 8 at a concentration of 0.1 wt. %. A portion (about ¼) of a magnetic disk, 2.5 inches in diameter, was dipped in each of the solutions and withdrawn at a rate of 4 mm/s to obtain a disk comprising a portion coated with one of the lubricant compounds 1 to 8 and an uncoated portion. The coated portions thus obtained were 32 angstroms in average thickness.

Each of the disks thus prepared was immediately attached to the ellipsometer and checked for variations in film thickness in the boundary between the coated portion and the uncoated portion at a specified time interval under the temperature condition of 50° C. to obtain the mono-layer thickness of the lubricant as the film thickness of the terrace portion to be provided.

Also used for comparison were Compound 9 having hydroxyl only at a molecular terminal, and Compound 10 having hydroxyl in the molecular chain and at a molecular terminal.

$$HOCH_2CH(OH)CH_2OCH_2CF_2O(CF_2CF_2O)x(CF_2O)yCF_2CH_2OCH_2CH(OH)CH_2OH \quad \text{(Compound 9)}$$

(wherein x is 10.1 and y is 10.9)

$$HO-(CH_2-R^2-CH_2O-E-O)_p-CH_2-R^2-CH_2-OH \quad \text{(Compound 10)}$$

E is a group represented by $-CH_2-CH(OH)-CH_2-$
$R^2$ is $-CF_2O(CF_2CF_2O)x(CF_2O)yCF_2-$
(wherein p is 2, x is 9.9 and y is 8.9)

Table 1 shows the evaluation of decomposition resistance and mono-layer thickness measurements. These results indicate that the perfluoropolyether compounds of the invention having an aromatic group and hydroxyl have higher decomposition resistance and a smaller mono-layer thickness than the compound 5 having hydroxyl only at the molecular terminal and compound 6 having hydroxyl in the molecule and at the molecular terminal.

TABLE 1

| Specimen | Mono-layer thickness (Å) | Ratio of decrease in weight (%) with $Al_2O_3$ | Ratio of decrease in weight (%) without $Al_2O_3$ |
| --- | --- | --- | --- |
| Compound 1 (Example) | 9 | 6 | 5 |
| Compound 2 (Example) | 11 | <1 | <1 |
| Compound 3 (Example) | 10 | 2 | 2 |
| Compound 4 (Example) | 11 | <1 | <1 |
| Compound 5 (Example) | 9 | 7 | 6 |
| Compound 6 (Example) | 10 | 2 | <1 |
| Compound 7 (Example) | 11 | 4 | 3 |
| Compound 8 (Example) | 13 | 5 | 4 |
| Compound 9 (Com. Ex.) | 21 | 97 | 37 |
| Compound 10 (Com. Ex.) | 13 | 98 | 30 |

Example 11

Preparation of Magnetic Disk

Each of Compounds 1 to 8 obtained in examples was dissolved in Vertrel-XF, product of DuPont. The solution was 0.1 wt. % in the concentration of Compounds 1 to 8. A magnetic disk, 2.5 inches in diameter, was immersed in the solution for 1 minute and then withdrawn at a rate of 2 mm/s. The disk was thereafter dried at 150° C. for 10 minutes. The coated compound was thereafter checked by FT-IR for film thickness.

Table 2 shows the results. It was confirmed that the magnetic disk can be obtained which is coated with the present compound, and has higher decomposition resistance and a smaller mono-layer thickness.

TABLE 2

| Specimen | Film thickness (Å) |
| --- | --- |
| Compound 1 | 12 |
| Compound 2 | 14 |
| Compound 3 | 13 |
| Compound 4 | 14 |
| Compound 5 | 13 |
| Compound 6 | 14 |
| Compound 7 | 14 |
| Compound 8 | 15 |

EXPLANATION OF THE SYMBOL

1: substrate;
2: recording layer;
3: protective layer;
4: lubricant layer

The invention claimed is:

1. A compound of the formula (1)

$$C_6H_4-(O-Z-R-X)_2 \quad (1)$$

wherein Z is $-CH_2CH_2O-$ or $-CH_2CH(OH)CH_2O-$, R is $-CH_2CF_2CF_2CF_2O(CF_2CF_2CF_2CF_2O)_nCF_2CF_2CF_2CH_2-$, n is a real number of 0 to 20, X is $-OH$, $-O(CH_2)_mOH$, $-OCH_2CH(OH)CH_2OH$, $-OCH_2CH(OH)CH_2O-C_6H_5$ or $-OCH_2CH(OH)CH_2O-C_6H_4-OCH_3$, m is an integer of 1 to 6.

2. A compound as defined in claim 1 wherein n is a real number of 0 to 4, and m is an integer of 1 to 4.

3. A lubricant containing a compound of the formula (1)

$$C_6H_4-(O-Z-R-X)_2 \quad (1)$$

wherein Z is $-CH_2CH_2O-$ or $-CH_2CH(OH)CH_2O-$, R is $-CH_2CF_2CF_2CF_2O(CF_2CF_2CF_2CF_2O)_nCF_2CF_2CF_2CH_2-$, n is a real number of 0 to 20, X is $-OH$, $-O(CH_2)_mOH$, $-OCH_2CH(OH)CH_2OH$, $-OCH_2CH(OH)CH_2O-C_6H_5$ or $-OCH_2CH(OH)CH_2O-C_6H_4-OCH_3$, m is an integer of 1 to 6.

4. A lubricant as defined in claim 3 wherein n is a real number of 0 to 4, and m is an integer of 1 to 4.

5. A magnetic disk comprising at least a recording layer and a protective layer formed over a substrate, and a lubricating layer formed over the resulting surface, the lubricating layer containing a compound of the formula (1)

$$C_6H_4-(O-Z-R-X)_2 \quad (1)$$

wherein Z is $-CH_2CH_2O-$ or $-CH_2CH(OH)CH_2O-$, R is $-CH_2CF_2CF_2CF_2O(CF_2CF_2CF_2CF_2O)_nCF_2CF_2CF_2CH_2-$, n is a real number of 0 to 20, X is $-OH$, $-O(CH_2)_mOH$, $-OCH_2CH(OH)CH_2OH$, $-OCH_2CH(OH)CH_2O-C_6H_5$ or $-OCH_2CH(OH)CH_2O-C_6H_4-OCH_3$, m is an integer of 1 to 6.

6. A magnetic disk as defined in claim 5 wherein n is a real number of 0 to 4, and m is an integer of 1 to 4.

* * * * *